United States Patent [19]

Battiste et al.

[11] Patent Number: 5,110,214
[45] Date of Patent: May 5, 1992

[54] APPARATUS AND METHOD FOR EVALUATING THE PROPENSITY OF POLYMERS FOR SMOKING DURING PROCESSING

[75] Inventors: David R. Battiste; Kenneth W. Willcox, both of Bartlesville; Tommy J. Morgan, Ramona, all of Okla.

[73] Assignee: Phillips Petroleum Company, Bartlesville, Okla.

[21] Appl. No.: 549,881

[22] Filed: Jul. 9, 1990

[51] Int. Cl.$^5$ ............................................. G01N 25/00
[52] U.S. Cl. ........................................ 374/45; 422/80; 422/82.05; 374/8; 356/438; 356/439; 340/628; 73/19.01; 73/23.2
[58] Field of Search ............ 422/80, 68.1, 82.05, 422/901; 73/19.01, 23.2, 29.01; 374/43, 45, 47, 7, 8; 364/477, 498, 500; 340/603, 627-630; 356/438, 439

[56] References Cited

U.S. PATENT DOCUMENTS

| | | | |
|---|---|---|---|
| 3,620,675 | 11/1971 | Olson | 422/68.1 |
| 3,812,705 | 5/1974 | Boillot | 73/19.01 |
| 3,868,186 | 2/1975 | Paukert et al. | 356/207 |
| 3,883,309 | 5/1975 | Ishizawa et al. | 23/260 |
| 3,901,602 | 8/1975 | Gravatt | 356/114 |
| 3,927,977 | 12/1975 | Jacobs | 422/86 |
| 3,946,228 | 3/1976 | Biermann | 73/19.01 |
| 4,246,784 | 2/1981 | Bowen | 374/117 |
| 4,320,975 | 3/1982 | Lilienfeld | 356/364 |
| 4,697,450 | 10/1987 | Bachman et al. | 73/23.2 |
| 4,838,706 | 6/1989 | Coey et al. | 73/19.01 |

FOREIGN PATENT DOCUMENTS

| | | | |
|---|---|---|---|
| 4443748 | 2/1989 | Japan | 374/43 |
| 1308938 | 12/1989 | Japan | 73/23.2 |
| 4445892 | 10/1974 | U.S.S.R. | 374/43 |

Primary Examiner—William A. Cuchlinski, Jr.
Assistant Examiner—Diego F. F. Gutierrez
Attorney, Agent, or Firm—Richmond, Phillips, Hitchock & Umphlett

[57] ABSTRACT

An apparatus and method for determining the propensity of a polymer to emit smoke by measuring the smoke emitted when the polymer is melted and extruded. The polymer is heated to a molten state and extruded under controlled time conditions into a receptacle from which gaseous samples can be collected, then the gaseous samples from the receptacle are analyzed for smoke content to determine the propensity of the polymer to emit smoke.

15 Claims, 2 Drawing Sheets

FIG. 1

APPARATUS AND METHOD FOR EVALUATING THE PROPENSITY OF POLYMERS FOR SMOKING DURING PROCESSING

BACKGROUND OF THE INVENTION

This invention relates to determination of the propensity of polymers to emit smoke during processing.

Polymers can emit smoke during extrusion and blow molding. The amount of smoke emitted will vary, depending upon which polymers are being processed. Because of the need to protect employees and equipment, it would be useful to evaluate, before full scale production runs, the propensity of any given polymer to emit smoke during processing.

Current ways of determining smoking propensity such as HPLC or conventional use of smoke detection devices have limitations such as:
(1) length of time required for analysis;
(2) dependence upon indirect inference of smoke;
(3) large variability and operator specificity; and
(4) requirement for sampling to be done on full scale equipment, thus necessitating large samples.

SUMMARY OF THE INVENTION

It is an object of this invention to provide an apparatus and method for determining the propensity of a polymer for smoking during processing such as extrusion or blow molding.

In accordance with this invention a measured amount of a polymer is heated to the molten state and extruded under controlled time conditions into a receptacle from which gaseous samples can be collected; then the gaseous samples from the receptacle are analyzed for smoke content.

In one specific embodiment of this invention, the gaseous sample from the receptacle is analyzed in a monitor which has an electrical output connected to a meter which can be a data logger device or an integrator/chart recorder. A data logging device connected to the monitor output gives readouts of the maximum, minimum and average monitored value of each sampling.

In another embodiment of this invention, a voltage attenuator steps down voltage from the monitor to an integrator/chart recorder which provides a continuous charting of the monitored values during the course of each sample analysis.

Another embodiment of this invention provides an apparatus with which to practice this method.

BRIEF SUMMARY OF THE DRAWINGS

FIG. 1 is a schematic of the apparatus.

DETAILED DESCRIPTION OF THE INVENTION

Figure 2:
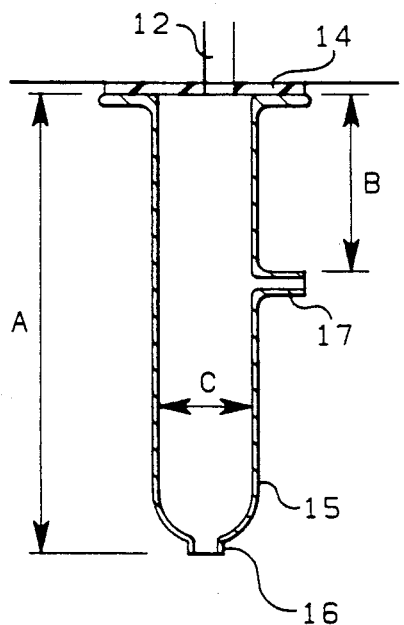
FIG. 2 gives an example of the smoke collection receptacle.

By melting and extruding a polymer under controlled time conditions and measuring the smoke thusly produced it is possible to predict the propensity of that polymer to produce smoke during full scale processing in extrusion or blow molding applications. This can be accomplished by use of an apparatus such as that described in this application.

Figure 1:
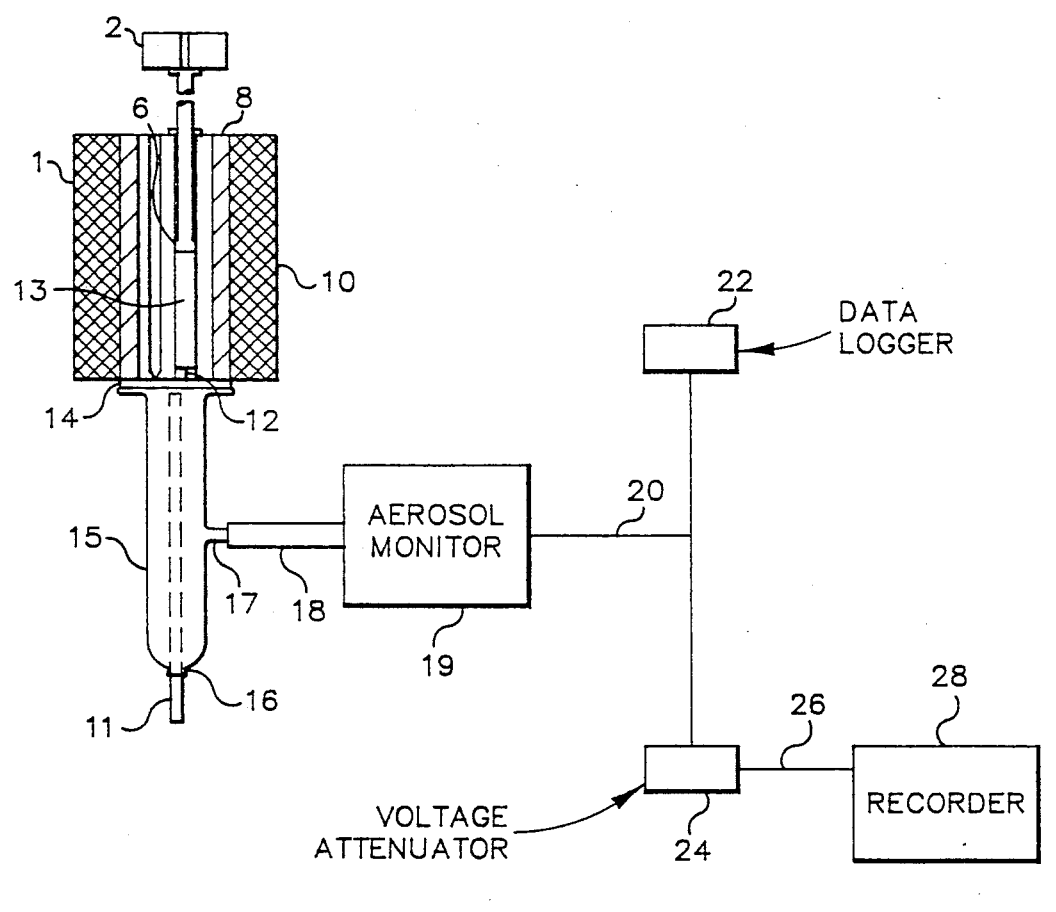

Referring to FIG. 1, a small extrusion device which for convenience can be a standard melt indexer comprises a thermostatically controlled heated cylinder 13 with an orifice 12 at the lower end and a weighted piston 6 operating within the cylinder. An amount of polymer in the form of pellets or granules is pre-measured. Rather than pre-measuring the amount of polymer, optionally other means of determining the amount being sampled can be used. For example, the length of extrusion time can be selected such that when a given weight of polymer of a known density is extruded, the amount of polymer can be readily computed. Also, marks indicating length of travel of the piston (where a piston is used) can be used to indicate the volume extruded.

The polymer is then heated to a molten state in the cylinder 13 of the melt indexer 1 for a fixed period by heater bands 8 which may optionally have a jacket of insulation 10. A weight 2 of appropriate mass is placed upon the piston 6, causing the piston 6 to extrude the polymer through the orifice 12 into a receptacle 15. Optionally an automated melt indexer or other rheometer may be used to melt and extrude the polymer.

The essential parameters to a meaningful analysis are the amount of polymer, the temperature of the extrusion, and the time. While any size apparatus could be used, it is more convenient to use a small sized apparatus such as a standard melt index machine or commercial capillary rheometer.

Figure 3:
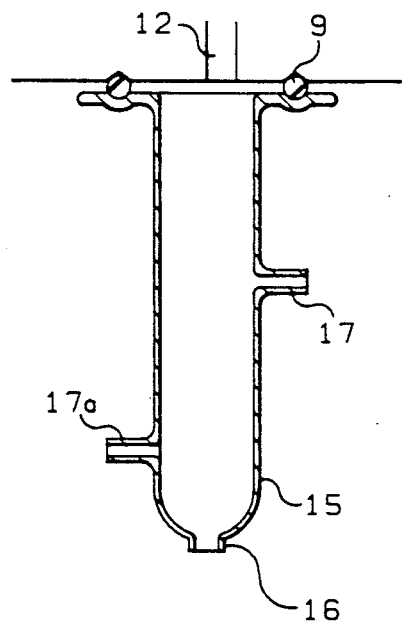
FIG. 3 shows an optional means of sealing the smoke collection receptacle to a melt indexer.

The receptacle 15 is large enough to provide a space surrounding the extrudate. The receptacle can be made of glass, metal or other appropriate substances. It can be fastened to the melt indexer 1 magnetically or by mechanical means such as screws or bolts. A TEFLON ® tape sealer 14, as shown in FIG. 2, can be used to sealingly mount the melt indexer to the receptacle; or particularly in the case of a metal tube, an O-ring 9, as shown in FIG. 3, or metal seal may be used. TEFLON ® is a polytetrafluoroethylene manufactured by E. I. DuPont De Nemours & Company, Wilmington, Del. The receptacle 15 has an opening 16 in the lower end through which the extrudate 11 may pass and a side arm opening 17 connected by a tube 18 to an aerosol monitor 19. Alternatively, the receptacle could have another opening 17a (FIG. 3) at the lower end to purge the system or to create a negative air flow prior to the extrusion. Where a gas is present, it is generally air for convenience and because it more accurately simulates most full-scale commercial molding operations. If desired, a countercurrent flow of gas could be used to sweep the smoke created toward the analyzer. Tests can be run in air and in an inert atmosphere to test the effect of the atmosphere on smoking.

One example of a receptacle is shown in FIG. 2. The receptacle 15 is made from glass and was fashioned using known glass blowing techniques. The receptacle 15 has an overall length A of 125±50 mm. The wall thickness of the receptacle 15 is about 6±0.5 mm and the inside diameter is about 25±5 mm. The receptacle 15 has a side arm type opening 17 with an inside diameter of about 4±1 mm. The side arm opening 17 is about 30±10 mm below the top of the receptacle 15. The lower opening at the bottom of the receptacle 15 is about 18±8 mm in diameter.

FIG. 2 shows a seal 14 between the top of the receptacle 15 and the lower face of the melt indexer 1. FIG. 3 shows an adaptation of the lower face of the melt indexer 1 and the top lip of the receptacle 15 to accommodate an O-ring seal 9.

Air is drawn from the receptacle 15 through the tube 17 into the aerosol monitor 19 for analysis of smoke content. Smoke analysis can be accomplished by use of optical means, such as visible light, infrared light, ultra violet light, or lasers such as helium or neon. Alternatively, other smoke detection means may be used.

An output signal representing the concentration of smoke sampled by the aerosol smoke monitor 19 is transmitted through appropriate readout circuitry for display of maximum, minimum and average levels by a data logger 22. The output signal from the aerosol monitor 19 may alternatively or additionally be transmitted through appropriate circuitry for continuous signal level recording and integration of the area under the charted peaks by an integrator/chart recorder 28.

A voltage attenuator 24 may be required in the electrical connection 20 and 26 between the aerosol monitor 19 and the integrator/chart recorder 28 to condition the current for actuating the integrator/chart recorder 28.

The readouts from the data logger 22 and the integrator/chart recorder 28 provide information which can be quantitatively compared for samples of polymers having different chemical compositions and/or different particle sizes to evaluate the relative propensity of the polymers to emit smoke during processing.

EXAMPLE

Equipment

In this example, the Aerosol Monitor utilized was a Model RAM-1 manufactured by Monitoring Instruments for the Environment, 213 Burlington Road, Bedford, Mass. 01730. The Personal Data Logger is a Model PDL-1 manufactured by GCA Corporation, Technology Division, 213 Burlington Road, Bedford, Mass., 07130. The Melt Indexer is a Tinius Olsen by the Tinius Olsen Testing Co., Easton Road, P.O. Box 429, Willow Grove, Pa., 19090. The special glass tube used with the Melt Indexer is as per FIG. 2 and was obtained from Phillips Petroleum Co., Glass Blowing Shop, Phillips Research Center, Bartlesville, Okla., 74004. The Integrator is a Hewlett-Packard, Model 3392A, Hewlett-Packard Company, 930 East Campbell Road, Richardson, Tex., 75081. Neoprene rubber hose, ¼" diameter×30" long was used to connect the glass sample tube with the monitor.

Samples

The polymers tested for this example were: polyethylene, designated C656, a resin made at a Pilot Plant, R & D Facilities, Phillips Petroleum Co., Bartlesville, Okla., 74004; polyethylene resins designated 5502 and Development Reactor (Dev. Rx) available from Phillips Petroleum Co., Plastics Division, Plastic Resins, Houston Chemical Complex, P.O. Box 792, Jefferson Road, Pasadena, Tex., 77501; and ALATHON®, a polyethylene resin by the E. I. DuPont De Nemours & Company, Wilmington, Del.

Procedure

With reference to FIG. 1, with the RAM-1 18 on and the glass tube in place, the Tinius Olsen Melt Indexer was set and maintained at 217° C. (422.6° F.) for one hour. The melt indexer 1 and orifice 12 were cleaned and the glass tube quickly replaced. The C656 polyethylene was thoroughly blended by shaking in a plastic cup and then 7.00±0.05 grams was weighed out. With the RAM-1 18 draft tube opening closed, the output reading was less than 1.00 prior to starting the test. The polymer was loaded and compacted well with the melt indexer rod member 6. A 2060 gram weight was positioned on the melt indexer rod 6 and inserted in the melt indexer 1 while simultaneously starting a stopwatch. The rod was manually pushed down with hand pressure on the weight 2 until approximately ¼ inch (0.635 cm) of polymer was extruded from the orifice 12. Then the 2060 gram weight 2 was allowed to remain in place for one minute, then removed. A larger weight capable of extruding the polymer in 2 minutes±5 seconds was selected. Then the polymer was allowed to heat up for 4 minutes and 55 seconds, or 5 minutes 55 seconds from the start of the stopwatch. At this 5 minute 55 second mark, the integrator 28 was started. At the six minute mark, the larger weight 2 was let down onto the rod 6 and polymer to extrude the polymer. At the 6 minute 10 second mark, the PDL-1 22 was turned on and set to receive data. At the 6 minute 30 second mark, data from the RAM-1 18 was admitted to the PDL-1 22. When the weight 2 and rod 6 traveled to its end on the melt indexer 1, the weights were left in place. The timer was stopped and data collection to the PDL-1 22 was terminated after 9 minutes of total time elapsed from when the stopwatch was started.

Results

The results of this example test are shown in TABLE I below.

TABLE I

| | PHYSICAL PROPERTIES | | | |
|---|---|---|---|---|
| Polymers | Pilot Plant C656 | Dev. Rx Feb. 87 | 5502 | DuPont Alathon |
| TEB (ppm) | 1 | 6 | 0 | — |
| Density (g/cc) | 0.959 | 0.956 | 0.957 | 0.959 |
| HLMI | 32 | 31 | 31 | 36 |
| HLMI/MI | 188 | 184 | 117 | 103 |
| Bottle ESCR (Purex bleach @ 140° F.) | 150 | 105 | 240 | 115 |
| Top Load, lb/f | 143 | 124 | 126 | 122 |
| Average Smoke (mg/m3) | 34 | 107 | 3 | 3 |

While this invention has been described in detail for the purpose of illustration, it is not to be construed as limited thereby but is intended to cover all changes and modifications within the spirit and scope thereof, including substitution of equivalents.

That which is claimed is:

1. An apparatus for determining the propensity of polymers to emit smoke comprising:
   (a) a means to heat said polymer to a molten state;
   (b) connected therewith a means to extrude said polymer after said polymer has reached said molten state;
   (c) a means for receiving the thus extruded polymer having an inlet end connected to said means to extrude so that said polymer enters said means for receiving through said inlet end after extrusion; and
   (d) a means to monitor gases from said means for receiving said extruded polymer and to determine the propensity of said extruded polymer to emit smoke by determining the presence and amount of smoke in said monitored gases, said means to monitor gases being in fluid communication with said means for receiving.

2. An apparatus as recited in claim 1 wherein there is:
a meter means connected to said means to monitor gases for displaying the magnitude of a signal from said means to monitor gases.

3. An apparatus as recited in claim 2 wherein said meter means has the capability of storing and displaying the maximum, minimum and average intensity of smoke in said monitored gases.

4. An apparatus as recited in claim 1 further having a means for integrating and recording a continuous signal from said means to monitor gases.

5. An apparatus as recited in claim 4 wherein said apparatus has a voltage attenuator means between said means to monitor gases and said integrating and recording means.

6. An apparatus as recited in claim 5 having a meter means connected to said means to monitor gases for displaying the magnitude of a signal from said means to monitor gases and said meter means having the capability of storing and displaying the maximum, minimum and average intensity of smoke in said monitored gases.

7. An apparatus as recited in claim 6 wherein said means for receiving said extruded polymer is a side-arm tube with an open outlet end and a side-arm with an opening therein; and
wherein said means to monitor gases has an optical sensing assembly and said means to monitor gases is connected to said opening in said side-arm tube.

8. An apparatus as recited in claim 1 wherein said means to heat said polymer and to extrude said polymer is a melt indexer.

9. An apparatus as recited in claim 1 wherein said means for receiving said extruded polymer is a side-arm tube having a side-arm with an opening therein and said opening in said side arm is connected to said means to monitor gases.

10. A method for determining the propensity of a polymer to emit smoke during processing comprising:
(a) heating said polymer to a molten state;
(b) extruding said polymer after said polymer has reached said molten state into an enclosed space;
(c) sampling gases from said enclosed space when said polymer is extruded into said enclosed space;
(d) monitoring said thus sampled gases for presence and amount of smoke in a monitoring device; and
(e) determining the propensity of said polymer to emit smoke.

11. A method as recited in claim 10 further comprising electrically communicating signals from said monitoring device to a data logger means.

12. A method as recited in claim 10 wherein continuous signals are communicated from said monitoring device to an integrator/chart recorder means and wherein said monitoring device is an aerosol monitoring device.

13. A method as recited in claim 12 wherein electrical signals from said aerosol monitoring device are attenuated prior to reception by said integrator/chart recorder means.

14. A method as recited in claim 13 wherein signals from said aerosol monitoring device are electrically communicated to a data logger means; and
wherein said data logger means displays the maximum, minimum and average levels of smoke intensity monitored in each sample of gases.

15. A method as recited in claim 10 wherein step (c) comprises drawing said gases from said enclosed space into said monitoring device so that a flow of said gases toward said monitoring device is created such that said flow draws more gases into said enclosed space.

* * * * *